United States Patent [19]
Sparks

[11] Patent Number: 5,823,996
[45] Date of Patent: Oct. 20, 1998

[54] INFUSION BALLOON CATHETER

[75] Inventor: Kurt D. Sparks, Miami, Fla.

[73] Assignee: Cordis Corporation, Miami Lakes, Fla.

[21] Appl. No.: 608,641

[22] Filed: Feb. 29, 1996

[51] Int. Cl.⁶ .................................................. A61M 29/00
[52] U.S. Cl. .............................. 604/96; 604/101; 604/53
[58] Field of Search ............................... 604/96, 101, 93, 604/102, 48, 53

[56]  References Cited

U.S. PATENT DOCUMENTS

| | | |
|---|---|---|
| 4,824,436 | 4/1989 | Wolinsky . |
| 4,994,033 | 2/1991 | Shockey et al. . |
| 5,000,734 | 3/1991 | Boussignac et al. . |
| 5,049,132 | 9/1991 | Shaffer et al. . |
| 5,087,244 | 2/1992 | Wolinsky et al. . |
| 5,098,381 | 3/1992 | Schneider . |
| 5,213,576 | 5/1993 | Abiuso et al. ............................ 604/96 |
| 5,232,444 | 8/1993 | Just et al. . |
| 5,254,089 | 10/1993 | Wang . |
| 5,269,755 | 12/1993 | Bodicky . |
| 5,279,565 | 1/1994 | Klein et al. . |
| 5,286,254 | 2/1994 | Shapland et al. . |
| 5,295,962 | 3/1994 | Crocker et al. . |
| 5,306,250 | 4/1994 | March et al. . |
| 5,318,531 | 6/1994 | Leone ........................................ 604/96 |
| 5,368,566 | 11/1994 | Crocker . |
| 5,397,307 | 3/1995 | Goodin . |
| 5,415,636 | 5/1995 | Forman . |
| 5,421,826 | 6/1995 | Crocker et al. . |

*Primary Examiner*—Michael Powell Buiz
*Assistant Examiner*—N. Kent Gring
*Attorney, Agent, or Firm*—Watts, Hoffmann, Fisher & Heinke Co., L.P.A.

[57] ABSTRACT

Apparatus and method is disclosed relating to an infusion catheter for treating a subject region with a treatment solution. A guide catheter allows the infusion catheter to be inserted into the subject and placed near a treatment region within the vascular system. A solution source is used to selectively inflate an infusion device. A passageway in the catheter body extends to an infusion device which has inner and outer chambers. Holes in a wall of the inner chamber route solution into the outer chamber and holes in the wall of the outer chamber route the solution into a subject vasculature. Solution pressure in the inner chamber is greater then the solution pressure in the outer chamber due to the relatively greater area of the holes in the outer chamber wall.

17 Claims, 4 Drawing Sheets

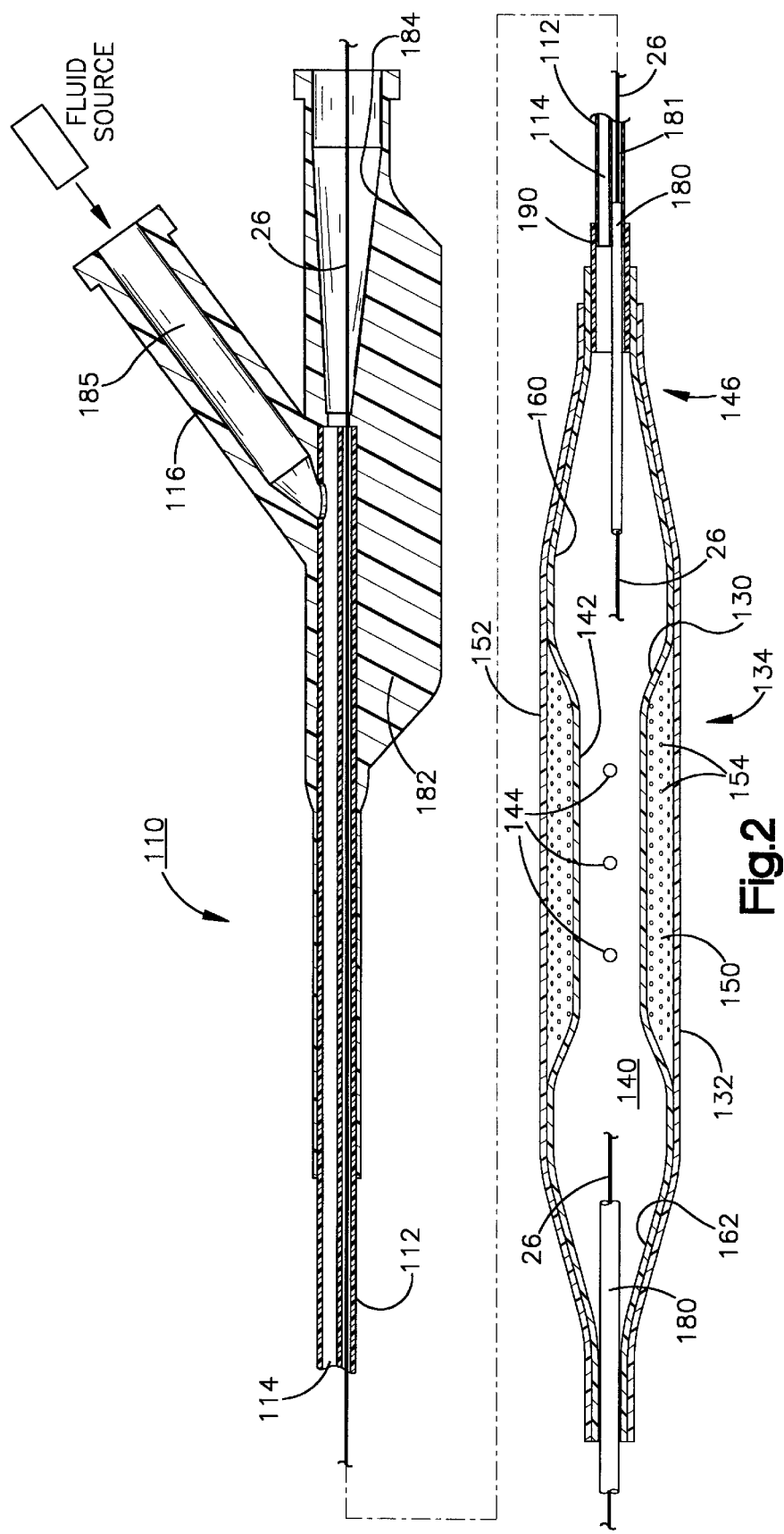

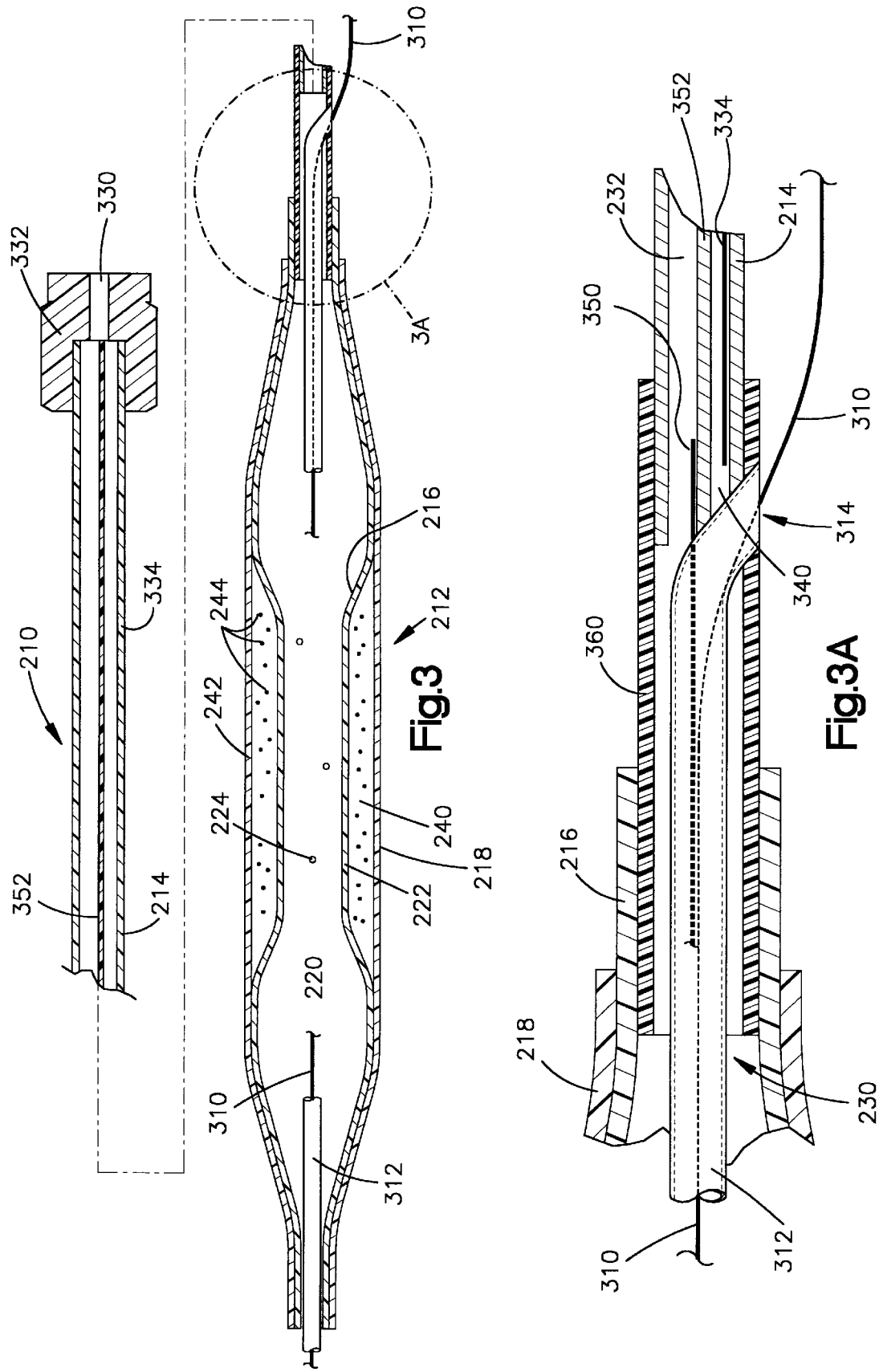

INFUSION BALLOON CATHETER

FIELD OF THE INVENTION

The present invention concerns an infusion balloon catheter for delivering a solution to a treatment site within a subject.

BACKGROUND ART

Catheterization procedures are well known for diagnosis and treatment of lesions in the cardiovascular system. One such catheterization procedure is known as angioplasty and is used to reduce the damaging effects of vascular plaque blockage or constriction in a subject blood vessel.

In an angioplasty procedure, an expandable balloon is introduced into the patient's arterial system and advanced until it is positioned in the region of the blockage or constriction. Once the balloon is properly positioned, it is expanded by filling it with a liquid. In successful procedures, the expandable balloon presses outwardly against the walls of the artery and expands the artery to increase blood flow.

Infusion catheters are catheters having an infusion balloon designed to deliver a solution to a treatment site within a blood vessel. The infusion balloon is placed at a subject treatment site in a manner similar to the process of placing a dilation catheter. The infusion balloon has openings in its side wall so that as medication is forced into the balloon from outside the subject it exits the balloon and is delivered into the blood vessel.

An infusion catheter may be used in conjunction with an angioplasty procedure to re-establish normal blood flow in a blood vessel and may be used by itself to administer solutions to a local area.

Examples of prior art patents relating to infusion catheters are U.S. Pat. No. 5,087,244 to Wolinsky, U.S. Pat. No. 5,232,444 to Just et al., U.S. Pat. No. 5,049,132 to Shaffer et al., U.S. Pat. No. 5,213,576 to Abiuso et al., and U.S. Pat. No. 5,318,531 to Leone. The disclosures of the Abiuso et al and the Leone patents are incorporated herein by reference.

The present invention concerns an improved infusion catheter designed to help control the delivery of medication into the subject blood stream.

SUMMARY OF THE INVENTION

An infusion catheter constructed in accordance with the present invention is used for local delivery of solutions within a subject vasculature. An example of a typical solution used for such treatment is heparin, which is an anticoagulant.

Apparatus constructed in accordance with the present invention includes an elongated catheter body for delivering a solution to an infusion site within a subject. The elongated catheter body defines a lumen extending from a proximally located solution input port to a region of an infusion balloon. The infusion balloon is most preferably attached to the elongated catheter body at a distal end of the elongated body.

A preferred infusion balloon includes an inner chamber having openings spaced along a wall of the inner chamber and has a solution entry portion in communication with the lumen that passes through the elongated body. Inflation or treatment solution is forced through the lumen from outside a subject into the inner chamber. An outer chamber has solution delivery openings in an outer wall and is attached to the inner chamber.

Most preferably the outer chamber overlaps a portion of the inner chamber wall through which solution exits the inner chamber to pass into the outer chamber or plenum. Solution in this plenum in turn passes through delivery openings in the outer chamber's outside wall to enter the subject. In accordance with one aspect of the invention, the total area of the openings in the outer balloon is greater than the total area of the openings in the inner balloon. This relationship means that the inner balloon becomes fully inflated and controls the amount of solution flow into the outer balloon. This relationship also means that the pressure of solution within the inner balloon is higher than the pressure of the solution that passes from the inner balloon to the outer balloon.

These and other features of the invention will be better understood from a detailed description of alternate embodiments of the invention which are described in conjunction with the accompanying drawings.

BRIEF DESCRIPTION OF THE DRAWINGS

FIG. 2 is a schematic depiction of a first embodiment of an infusion catheter constructed in accordance with the present invention;

FIG. 3 is a schematic depiction of a second embodiment of an infusion catheter constructed in accordance with the present invention; and FIG. 3A is an enlarged section view of a guidewire tube portion of the FIG. 3 catheter.

DETAILED DESCRIPTION OF THE PREFERRED EMBODIMENTS

Figure 1:
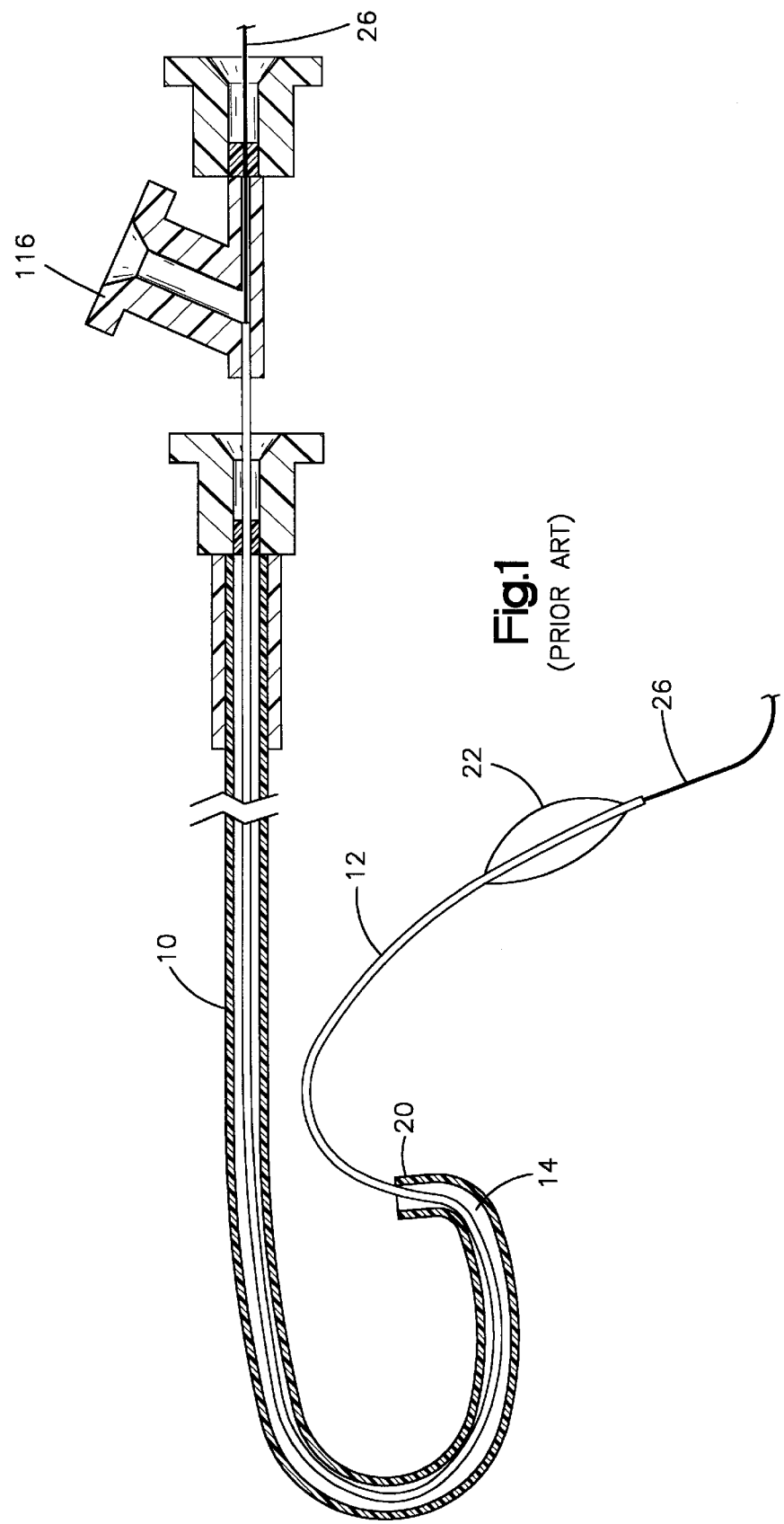
FIG. 1 is a schematic depiction of a guide catheter routing a balloon catheter (either an infusion or a dilation catheter) to a treatment site within a subject blood vessel.

FIG. 1 illustrates use of a guide catheter 10 for positioning a balloon catheter 12 within a subject blood vessel. The guide catheter 10 includes an elongated body having a central passageway 14 that extends from a connector 16 outside the subject through the body and out the distal end 20 of the guide catheter. In most applications, the guide catheter 10 is advanced until the guide catheter's distal end 20 reaches a position within the subject's cardiovascular system close to a treatment region. The treatment region can be the location of a lesion that is to be compressed or can be the location for delivery of a treatment solution such as heparin. In the former instance a balloon 22 treats the lesion by coming into contact with it and compressing it. In the latter instance the balloon 22 is only positioned within the blood vessel for delivery of a treatment solution.

Positioning of the balloon 22 is performed with the aid of a guidewire 26. The guidewire 26 is pushed through a center lumen (not shown) of the catheter 12 until the guidewire tip extends a few centimeters beyond the catheter's distal tip. The combination of the guidewire 26 and the balloon catheter are inserted into the guide catheter 12 until the end of the guidewire exits the guide catheter. Both the guidewire 26 and the balloon 22 are pushed forward until the guidewire tip extends beyond the treatment region and the balloon catheter is properly positioned. Positioning of the balloon is facilitated by use of a marker member attached to the catheter that can be viewed on a monitor by an attending physician. The present invention is principally concerned with use of the disclosed embodiments of the invention for delivering a treatment solution to a treatment region.

FIG. 2 depicts an infusion catheter 110 for injecting a solution into a subject. The catheter includes an elongated, dual lumen catheter body 112 for delivering a solution to an infusion site within a subject. A first lumen 114 extends from a proximally located solution input port 116 to a distal end of the elongated body 112.

Attached to the distal end of said elongated, dual lumen catheter body 112 are inner and outer solution confining balloons 130, 132 that define a solution delivery member 134. A first balloon 130 bounds an inner chamber 140. A center wall portion 142 has equally spaced openings or holes 144. At a proximal end of the infusion balloon 134 the two balloons 130, 132 overlap an end of the catheter body 12 to form a fluid entryway or opening 146 in fluid communication with the lumen 114 passing through the elongated body 112. Fluid injected into the sideport 116 passes through the lumen 114 from outside a subject into the inner chamber 140 by means of the entryway 146.

An outer chamber or plenum 150 is bounded by a wall 152 of the second balloon 132. The outer chamber 150 is also bounded by an outer surface of the wall 142 that defines the inner chamber 140. The wall 152 includes solution delivery openings 154 spaced along the length of the plenum 150. Solution exits the inner chamber to the outer chamber by means of holes 144, passes through the outer chamber 150 and is delivered to the vessel through the delivery openings 154 in the wall 152.

In accordance with a preferred embodiment of the invention, the inner balloon 130 has two solution confining chambers or lobes 160, 162 connected to each other by the center wall portion 142. A first lobe 160 is attached to the distal end of the elongated body to form the solution entry opening 146 of the inner chamber. In this embodiment the openings 144 for allowing solution to pass from the inner chamber to the outer chamber are located along the center wall section 142 and not along wall defining sections of the lobes.

In the embodiment illustrated in FIG. 2, a guidewire tube 180 extends completely through the inner chamber 140 from outside the catheter's distal end into a second lumen 181 of the dual lumen catheter body. Outside the subject this lumen 181 opens into an inlet port 184 of a molded plastic hub 182 that also defines the side port 116 for injecting fluid through a passageway 185 into the lumen 114.

Figure 2A:
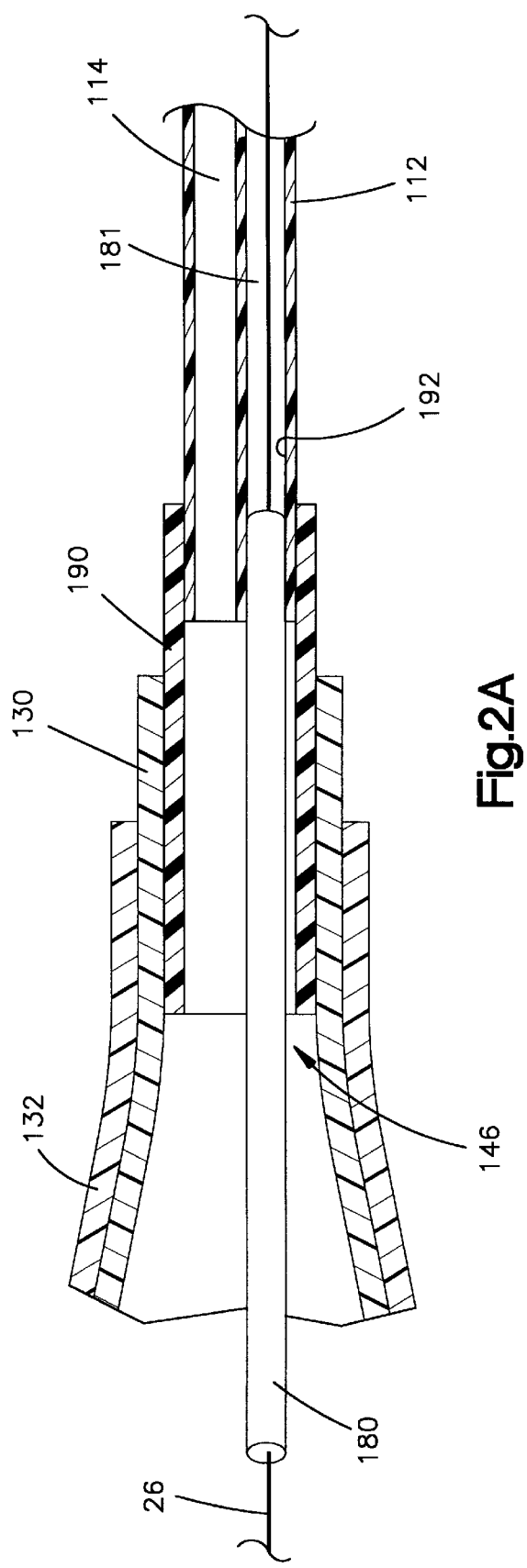
FIG. 2A is an enlarged section view of a transition seal region of the infusion catheter of FIG. 2.

Engagement between the elongated body 112 and the balloons 130, 132 is more clearly depicted in the enlarged view of FIG. 2A. An outer body 190 overlaps the dual lumen body 112 and is contacted by the proximal end of the inner balloon 130. The tube 180 is connected to dual lumen body 112 by inserting a proximal end of the tube 180 into the lumen 181 and sealing the tube to an inner wall 192 of the lumen 181. As seen in FIG. 2 the tube 180 extends through the balloons 130, 132 and is fused to the inner balloon 130 near a distal end of the catheter. A preferred guidewire tube 180 is a co-extruded tube having an inner, relatively thin layer of lubricous material and a stiffer, thicker outer layer. Prior art catheters sold by Cordis Corporation have included guidewire tubes of such a construction.

Representative diameter sizes for the holes in the inner and outer chamber walls are 25 microns for the openings 144 in the inner balloon and 8 microns for the openings 154 in the outer balloon. To assure that the outer chamber is at a much lower pressure than the inner chamber, the outer chamber has many more holes in its outer wall. Infusion catheters constructed in accordance with the invention have balloon diameters of from approximately 2.5 to 4 millimeters when inflated. A pressure of approximately three atmospheres is maintained at the proximal hub 182 throughout solution delivery into the subject vasculature.

The inner and outer chambers are connected together at the locations the balloons 130, 132 are attached to the catheter body 112 and the guidewire tube 180. The two balloons 130, 132 are in overlying relation to each other along the length of the balloon but are not connected along their lengths.

A second embodiment of a rapid exchange infusion catheter 210 is depicted in FIG. 3. In this embodiment the catheter also includes an infusion balloon 212 attached to an elongated catheter body 214 at a distal end of the elongated body. The infusion balloon 212 is made up of inner and outer balloons 216, 218. An inner chamber 220 is bounded by the inner balloon 216 and has a center wall portion 222 that include holes 224 spaced along the center wall portion 222.

A solution entry opening 230 is in communication with a lumen 232 of the elongated body. This lumen 232 routes solution from outside a subject into the inner chamber 220. An outer chamber 240 has an outer wall 242 defined by the balloon 218 that includes solution delivery openings 244. The solution delivery openings in the outer balloon are axially co-extensive with the center wall portion 222 of the inner balloon having the holes 224. The openings 244 in the outer chamber's outer wall deliver solution into the vasculature.

The second embodiment of the invention illustrated in FIGS. 3 and 3A also contemplates use of a guidewire 310. A generally cylindrical tube 312 passes through the center of the inner balloon chamber 220 and exits the infusion catheter 210 at a region proximal to the balloon 212 by passing through a side opening 314 in the catheter body. This allows for rapid exchange of the catheter with a similar catheter of slightly different dimension without withdrawing the guidewire. To exchange catheters, the guidewire 310 is held stationary and the catheter is withdrawn over the guidewire until the balloon exits from the guide catheter. A portion of the guidewire distal to the balloon can then be grasped by an attending physician and an alternate catheter pushed over the guidewire to position an infusion balloon at a treatment site.

The catheter shown in FIG. 3 has a single inflation port 330 defined by a connector 332 attached to a proximal end of the catheter body. Since the FIG. 3 catheter is a rapid exchange catheter, no portion of the guidewire extends through the part of the catheter body proximal to the side opening 314. A metal stiffening wire 334 is used to add stiffness to the catheter body which is proximal to a region of the transition seal. This wire 334 extends from the proximal end of the catheter body to a point just behind the side opening 314 through which the guidewire 310 exits the catheter.

The region of the catheter body that is proximal to the side opening 314 has two lumens or passageways. A first passageway or lumen 232 routes solution to the balloon. The stiffening wire 334 extends through a second lumen 340 from a point near the hub 332 to a distal end of the lumen 340. This wire is fixed in place (typically by fusing) within the catheter body. Since the FIG. 3 embodiment is a rapid exchange catheter, the second lumen 340 can be closed at both ends. As seen in the FIG. 3 one end of the lumen 340 is closed by the hub 332.

As seen most clearly in FIG. 3A, a support wire 350 (typically metal) is attached to the inside wall of the lumen 232. The inner balloon 216 is attached (typically by either heat fusion or with an adhesive) to a tubular outer body 360 of that catheter body that defines the opening 314 through which the guidewire 310 exits the catheter. The outer balloon 218 is heat fused to the inner balloon 216 in the region the inner balloon is attached to the outer body 360. Although the inner and outer balloons are in contact along transition portions of the infusion member, they are not fused but instead merely overlie one another except in the short region they are fused together at the ends. The outer body 360 is constructed from nylon as are the inner and outer balloons and the elongated tubing that defines the catheter body. The balloons could also be made from polyester. The body, balloon, and transition portions of the catheter are all formed by molding or extruding.

But for the presence of the bridging wire 350 embedded in the catheter which bridges the outer body 360 the catheter depicted in FIGS. 3 and 3A would tend to kink or bend back on itself at this transition region. The wire 350 tends to maintain the balloon extended away from the catheter body, so that pushing on the catheter from outside a subject causes the catheter to move further into the subject blood system rather than kinking.

Both the inner and outer balloons are fabricated from a parison which is a small diameter Nylon tube having an outer diameter of approximately 0.030 inch. A length of this parison is advanced into a mold, the inner surface of which defines the shape of the blown balloon. The mold is heated to a temperature which allows the parison to be expanded, while under pressure, to meet the contour of the inner surface of the mold. The blown parison is "heat set" to set the shape of the blown balloon as defined by the mold. The mold is subsequently cooled to allow the balloon to be pulled out of the mold, thus completing the fabrication process.

Holes having a nominal diameter of 25 microns are drilled through the inner balloon using a Yttrium Aluminum Garnet (YAG) laser. A laser beam is focused to a point source and the power of the beam is adjusted such that a single pulse of laser light vaporizes exactly a volume of nylon from the balloon to leave a nominal 25 micron diameter hole.

The outer balloon holes are also laser drilled, but are drilled using an Excimer laser. The method for drilling these holes is a modification from the method used for the inner balloon. The laser beam is passed through a "mask" before reaching the balloon to be drilled. This mask is a flat piece of specialized material which has an array of holes. Upon passing through the mask, the main beam is split into many smaller beams. A small beam is produced for each hole in the mask. A typical mask may contain from 5 to 100 holes. The result is that a single pulse of the main beam is effectively split into many smaller beams, each drilling its own hole in the balloon. These holes also follow the exact pattern of the mask. The method allows many holes to be drilled simultaneously, and a resultant large number of holes are drilled into a small object such as an angioplasty balloon.

The escape area of each balloon (the number and size of the holes) determines the relative internal pressure of one balloon to the other, since the solution flowrate through the outer balloon is exactly the same as that of the inner balloon. The inner balloon escape area is designed to be small compared to the escape area of the outer balloon. In accordance with a preferred embodiment of the invention the inner balloon has six holes with a diameter of from 25 to 40 microns. Based on a 25 micron diameter the escape area of the inner balloon is approximately 2945 square microns.

The outer balloon escape area is dependent upon the balloon diameter. The holes are typically drilled with a nominal spacing between each hole. Thus a larger balloon will have a greater surface area to drill additional holes when compared with a smaller balloon. For a 2.5 millimeter diameter balloon having approximately 1500 eight micron diameter holes the total escape area of the outer balloon can be calculated to be 75,000 square microns. For a 4 millimeter diameter balloon having 2400 eight micron diameter holes the total escape area of the outer balloon can be calculated to be 120,000 square microns. For these two examples the ratio of escape area of the outer balloon to the inner balloon is either 25:1 or 40:1.

Experience with an infusion catheter constructed in accordance with the present invention suggests certain ranges of values for the holes for the inner and outer balloon. The total area of the holes in the inner balloon should be approximately in the range 500 to 10,000 square microns for catheters of diameter of from 2.5 to 4 millimeters in diameter. The outer balloon for such catheters should have a total area from 5,000 to 1,000,000 square microns. The ratio between the area of the outer to inner balloon openings should be in the range of 10:1 to 2000:1.

Operation

Practice of the invention has a number of advantages. In operation, the infusion catheter is positioned at a treatment site. Infusion solution is injected into the catheter and passes through the catheter body to the inside of the inner balloon. The inner balloon maintains a high pressure relative to the outer balloon. The holes in the outer balloon are significantly greater in number than the holes in the inner balloon so that the effective escape area of the outer balloon is greater than the inner balloon, allowing the outer balloon to maintain a low pressure less than the high pressure of the inner balloon. A relatively low, controlled flow rate is achieved through both balloons while the inner chamber is maintained at a relatively high pressure.

Another characteristic of the illustrated catheter construction is that the outer balloon will not fold onto itself during catheter aspiration, by virtue of the greater escape area through the wall of the outer balloon. When pressurized solution is injected into the first and second lobes of the dogbone shaped inner balloon, the inner balloon will fully distend under the high pressure. This extension of the lobes fully expands the outer balloon to bridge the two lobes. Without this support the outer balloon cannot maintain a full distended shape due to the great escape area of the holes in the outer balloon. The plenum defined by the outer balloon provides mixing of the infusate along the working length of the outer balloon.

The infusion catheter's in-vivo flow rate will be regulated by the interface between the infusion element and the blood vessel wall, up to a maximum flowrate defined by the in-vitro flow rate. Therefore, the in-vivo flow rate may not exceed the maximum in-vitro flow rate as defined by the flow regulation of the inner balloon.

Turbulent flow through the inner balloon holes in the plenum provides substantial distribution of solution within the entire volume of the plenum and subsequent delivery through the porous outside working length of the plenum. At the recommended operating pressures of 45 psi the inner balloon regulation of flow limits the flowrate through each hole in the outer balloon to a rate below which inertial streaming from the outer balloon could occur.

While the present invention has been described with a degree of particularity, it is the intent that the invention include all modifications and alterations from the disclosed design falling within the spirit or scope of the appended claims.

We claim:

1. An infusion catheter for injecting a solution into a subject comprising:

a) an elongated catheter body for delivering a solution to an infusion site within a subject including a lumen extending from a proximally located solution input port of the elongated body to a distal end of the elongated catheter body; and b) an infusion member attached to the elongated catheter body at a distal end of said elongated catheter body; said infusion member defining i) an inner chamber having a chamber defining wall that includes a first set of holes spaced along said chamber defining wall and further having a solution entry in communication with the lumen of the elongated catheter body for routing solution passing through the lumen from outside a subject into the inner chamber and ii) an outer chamber having an outer chamber wall that includes a second set of holes having a greater total area than the area of the first set of holes in the chamber defining wall of the inner chamber, and where the outer chamber is supported adjacent to the inner chamber to overlap a portion of the inner chamber wall through which solution exits the inner chamber to the outer chamber by means of the first set of holes to pass through said second set of holes and enter the subject.

2. The infusion catheter of claim 1 where the inner chamber of the infusion member is bounded by an inner balloon that includes two solution confining chamber lobes connected to each other by a center section interposed between the two lobes and wherein one of the two lobes is attached to the distal end of the elongated body to form the solution entry opening of said inner chamber.

3. The infusion catheter of claim 2 wherein the outer chamber is bounded by an outer balloon that overlies an outer surface of the inner balloon and extends between the two lobes to define a solution delivery region between an inner surface of the outer chamber wall and an outer surface of the inner chamber wall.

4. The infusion catheter of claim 3 wherein an outer wall of the outer balloon is spaced from the center section of the inner balloon along the region of the center section that connects the two lobes of the inner balloon.

5. The infusion catheter of claim 1 additionally comprising a guidewire tube that extends through the infusion member and exits the infusion catheter through a side wall of the catheter body to accommodate a guidewire for use in helping position the infusion catheter within a subject vasculature.

6. The infusion catheter of claim 1 additionally comprising a guidewire tube that extends longitudinally through a center portion of the elongated catheter body and through a center of the infusion balloon to allow the guidewire to exit both a proximal and a distal end of the catheter.

7. The infusion catheter of claim 1 wherein the catheter body defines two side by side lumens and wherein one of said side by side lumens delivers solution to the infusion member and a second of the two side by side lumens is used to support a relatively rigid stiffening rod.

8. A method for constructing an infusion catheter comprising the steps of:

a) extruding a catheter body having an outer wall that bounds a solution delivery region through the catheter body;

b) providing an elongated guidewire tube having a diameter large enough to allow a guidewire to be pushed through the guidewire tube;

c) attaching the guidewire tube to the catheter body so that one end of the guidewire tube is exposed to allow a guidewire to be pushed into and through the guidewire tube for use in positioning the infusion catheter;

d) forming first and second flexible balloons and forming first and second sets of holes of different cross sectional area in side walls of said first and second flexible balloons by laser drilling said holes through a thickness of said first and second flexible balloons; and e) attaching one end of a first balloon having a set of holes with a relatively small total cross sectional area to the guidewire tube and attaching a second end of the first balloon to the catheter body to allow solution to flow down the length of the catheter body into the said first balloon and attaching a second balloon having a set of holes with a relatively larger total cross sectional area to the first balloon to enclose a solution delivery region between the first and second balloons.

9. The method of claim 8 wherein the first and second balloons are constructed of nylon and wherein said first and second balloons are attached to each other in overlying relation by heat fusing.

10. The method of claim 8 wherein holes are drilled through the wall of the first balloon by directing a laser beam at selected spots on a wall of the first balloon and wherein holes are drilled through the wall of the second balloon by directing a laser beam to a mask having a plurality of holes to form laser beam segments and directing the laser beam segments at the wall of the second balloon.

11. A method for local delivery of solutions within a subject vasculature comprising the steps of:

a) inserting a tubular guiding catheter into the vascular system of a subject;

b) providing an infusion catheter for insertion into the guiding catheter, said infusion catheter having an inner pressure regulating balloon including first and second solution confining lobes connected to each other by an intermediate center wall portion and an outer solution delivery balloon in overlying relation to the first and second lobes of the inner balloon; said inner balloon being attached to a catheter body to receive an amount of infusate injected at a proximal end of the infusion catheter at relatively high pressure and to transmit a controlled amount of infusate to an interior of the outer solution delivery balloon at lower pressure for delivery to a treatment site of a subject blood vessel;

c) inserting an elongated guidewire through a guidewire tube that passes through the inner and outer balloons of the infusion catheter;

d) positioning the infusion catheter relative to a treatment region of a blood vessel by pushing the combination of elongated guidewire and infusion catheter through the guide catheter; and e) injecting a controlled amount of inflation solution through the infusion catheter body to inflate said first and second lobes of said inner pressure regulating balloon thereby fully expanding the outer balloon to bridge the first and second lobes and delivering the controlled amount of infusate at the treatment site.

12. An infusion catheter for injecting a solution into a subject comprising:

a) an elongated catheter body for delivering a solution to an infusion site within a subject including a passageway extending from a proximally located solution input port of the elongated catheter body to a distal end of the elongated catheter body;

b) an infusion balloon attached to the elongated catheter body at a distal end of said elongated catheter body; said infusion balloon defining i) a relatively high pressure inner chamber having a chamber defining wall that includes a first set of holes spaced along said chamber defining wall and further having a solution entry in communication with the passageway of the elongated body for routing solution passing through the passageway from outside a subject into the inner chamber and ii) a lower pressure outer chamber having an outer wall that includes a second set of holes and is supported adjacent to the inner chamber to overlap a portion of the inner chamber wall through which solution exits the inner chamber to the outer chamber by means of the first set of holes to pass through said second set of holes and enter the subject; the total area of the first set of holes in the inner, higher pressure chamber being less than the total area of the second set of holes in the outer, lower pressure chamber; and c) solution injection means for injecting treatment solution into the catheter body for delivery to a treatment site in the subject.

13. The infusion catheter of claim 12 where a ratio of the total area of the second set of holes to the total area of the first set of holes in a range of from 10:1 to 2000:1.

14. The infusion catheter of claim 13 wherein the first set of holes have a total cross sectional area of between 500 and 10,000 square microns.

15. The infusion catheter of claim 13 wherein the second set of holes have a total cross sectional area of between 5000 and 1,000,000 square microns.

16. The infusion catheter of claim 12 wherein the individual holes in the first and second sets of holes are generally circular.

17. The infusion catheter of claim 12 where the high pressure inner chamber includes two solution confining chamber lobes connected to each other by a center section interposed between the two lobes and wherein one of the two lobes is attached to the distal end of the elongated body to form the solution entry of said inner, high pressure chamber.

* * * * *